(12) United States Patent
Nzike et al.

(10) Patent No.: US 9,592,347 B2
(45) Date of Patent: Mar. 14, 2017

(54) ASSEMBLY FOR A DRUG DELIVERY DEVICE, PISTON ROD AND DRUG DELIVERY DEVICE

(71) Applicant: Sanofi-Aventis Deutschland GmbH, Frankfurt am Main (DE)

(72) Inventors: Philippe Nzike, Frankfurt am Main (DE); Steffen Raab, Frankfurt am Main (DE); Uwe Dasbach, Frankfurt am Main (DE); Uwe Boeser, Frankfurt am Main (DE); Ulrich Brüggemann, Frankfurt am Main (DE); Francisco Soares, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 410 days.

(21) Appl. No.: 14/191,757

(22) Filed: Feb. 27, 2014

(65) Prior Publication Data

US 2014/0194830 A1    Jul. 10, 2014

Related U.S. Application Data

(63) Continuation of application No. 13/810,504, filed as application No. PCT/EP2011/063445 on Aug. 4, 2011, now abandoned.
(Continued)

(30) Foreign Application Priority Data

Sep. 2, 2010    (EP) .................... 10175000

(51) Int. Cl.
  *A61M 5/31*    (2006.01)
  *A61M 5/315*   (2006.01)
  *A61M 5/24*    (2006.01)

(52) U.S. Cl.
  CPC .... *A61M 5/31536* (2013.01); *A61M 5/31525* (2013.01); *A61M 5/31541* (2013.01);
(Continued)

(58) Field of Classification Search
  CPC ................ A61M 5/24; A61M 5/31525; A61M 5/31536; A61M 5/31541; A61M 5/31543;
(Continued)

(56) References Cited

U.S. PATENT DOCUMENTS

2009/0240195 A1    9/2009    Schrul et al.
2010/0036320 A1    2/2010    Cox et al.
2010/0087799 A1    4/2010    Galbraith et al.

FOREIGN PATENT DOCUMENTS

EP    1683538    7/2006
EP    1923083    5/2008
(Continued)

OTHER PUBLICATIONS

International Search Report for Int. App. No. PCT/EP2011/063445, completed Nov. 8, 2011.
(Continued)

*Primary Examiner* — Imani Hayman
(74) *Attorney, Agent, or Firm* — McDonnell Boehnen Hulbert & Berghoff LLP

(57) ABSTRACT

An assembly for a drug delivery device, comprising: a housing having a distal end and a proximal end, a piston rod, a drive member, the drive member being moveable in a proximal direction with respect to the housing and with respect to the piston rod for setting a dose of a drug, at least one stop member which is provided on one of the piston rod and the drive member and which is radially moveable with respect to the one of the piston rod and the drive member on which it is provided, and at least one interaction member which is provided on the other one of the piston rod and the
(Continued)

drive member. Furthermore, a piston rod for a drug delivery device is provided.

17 Claims, 7 Drawing Sheets

Related U.S. Application Data

(60) Provisional application No. 61/371,235, filed on Aug. 6, 2010.

(52) U.S. Cl.
CPC .... *A61M 5/31551* (2013.01); *A61M 5/31585* (2013.01); *A61M 5/24* (2013.01); *A61M 5/31543* (2013.01); *A61M 5/31593* (2013.01)

(58) Field of Classification Search
CPC .......... A61M 5/31551; A61M 5/31585; A61M 5/31593; B60K 17/356; B60K 6/387; B60K 6/442; B60K 6/52; B60K 6/547; B60K 7/0007; F16H 3/006; Y02T 10/6234; Y02T 10/6265
See application file for complete search history.

(56) References Cited

FOREIGN PATENT DOCUMENTS

| | | |
|---|---|---|
| JP | 2010-523183 | 7/2010 |
| WO | 2006/024461 | 3/2006 |
| WO | 2008/122360 | 10/2008 |
| WO | 2009/092807 | 7/2009 |

OTHER PUBLICATIONS

International Preliminary Report on Patentability for Int. App. No. PCT/EP2011/063445, mailed Feb. 21, 2013.
Japanese Office Action for JP App. No. 2013-522253, mailed Feb. 2, 2016.

ASSEMBLY FOR A DRUG DELIVERY DEVICE, PISTON ROD AND DRUG DELIVERY DEVICE

CROSS REFERENCE TO RELATED APPLICATIONS

The present application is a continuation of U.S. patent application Ser. No. 13/810,504, filed Jan. 16, 2013, which is a U.S. National Phase Application pursuant to 35 U.S.C. §371 of International Application No. PCT/EP2011/063445 filed Aug. 4, 2011, which claims priority to U.S. Provisional Patent Application No. 61/371,235 filed Aug. 6, 2010 and European Patent Application No. 10175000.8 filed Sep. 2, 2010. The entire disclosure contents of these applications are herewith incorporated by reference into the present application.

FIELD OF INVENTION

This disclosure relates to an assembly for a drug delivery device and a piston rod suitable to be integrated in a drug delivery device. Furthermore, a drug delivery device is disclosed.

BACKGROUND

In a drug delivery device, often, a bung is provided within a cartridge that contains a drug. The bung is displaced with respect to the cartridge for delivering a dose of the drug. It is desirable that the actually dispensed dose of the drug matches an intended dose which was previously set by a user as good as possible. This is to say, the device should have a high dose accuracy. Furthermore, it is expedient to prevent a dose setting action for setting a dose which may exceed the quantity of drug still present in the cartridge. Safety for a user may be increased in this way.

A drug delivery device is, for example, described in document EP 1 923 083 A1.

SUMMARY

It is an object of the present disclosure to provide an assembly facilitating provision of a novel, preferably an improved, drug delivery device, for example a device having high dose accuracy and/or with good user-safety.

This object may be achieved by the subject matter of the independent claims. Further features and advantageous embodiments are subject matter of dependent claims.

According to one aspect an assembly for a drug delivery device is provided. The assembly may comprise a drive mechanism for the device. The assembly may comprise a housing. The housing may have a distal end and a proximal end. The assembly may comprise a piston rod. The assembly may comprise a drive member. The drive member may be moveable in a proximal direction with respect to the housing and, preferably, with respect to the piston rod for setting a dose of a drug. The assembly may comprise at least one stop member. The stop member may be provided on one of the piston rod and the drive member. The stop member may be radially moveable with respect to the one of the piston rod and the drive member on which it is provided. The assembly may comprise at least one interaction member. The interaction member may be provided on the other one of the piston rod and the drive member. In a non-locking mode of the assembly, the stop member may be radially biased. The stop member and the interaction member may be arranged axially spaced apart from each other by an axial distance in the non-locking mode. The axial distance may be reduced by a dosing distance when the drive member is moved in the proximal direction, e.g. for setting a dose of the drug. When the dosing distance corresponds to the axial distance, the assembly may be configured to switch into a locking mode. For switching into the locking mode, the radial bias of the stop member is expediently permitted to decrease at least partially. The radial bias of the stop member may be decreased such that the stop member and the interaction member are brought in mechanical cooperation. When the stop member and the interaction member mechanically cooperate, the stop member and the interaction member are configured to permanently or releasably axially interlock the piston rod and the drive member. Consequently, in the locking mode, movement of the drive member with respect to the piston rod, in particular in the proximal direction with respect to the piston rod, may be prevented. In particular, a subsequent dose setting procedure is expediently prevented in the locking mode.

The assembly may be configured to switch from the non-locking mode into the locking mode when the maximum settable dose exceeds the quantity of drug still available in the device. Setting of a dose of the drug which exceeds the available quantity of the drug, may thus be prevented by mechanical cooperation of the interaction member and the stop member. Underdosing, which may have fatal or even lethal consequences for the user, may be prevented in this way. Hence, provision of a drug delivery device providing high safety for the user is facilitated.

A further aspect relates to a piston rod for a drug delivery device. The piston rod may comprise a, preferably resiliently mounted, member. The member may be arranged in a proximal end section of the piston rod. The member may be radially moveable with respect to the piston rod.

Preferably, the resiliently mounted member is secured against axial and/or rotational movement with respect to the piston rod. The resiliently mounted member may be adapted and arranged to assist prevention of movement of the piston rod for dispensing a dose of a drug exceeding the present quantity of the drug held in the drug delivery device.

A further aspect relates to a drug delivery device. The drug delivery device may comprise the assembly and/or the piston rod described above. The drug delivery device may comprise a cartridge. The cartridge may hold a plurality of doses of a drug. The assembly may provide an end-stop mechanism. The end-stop mechanism may be adapted to prevent setting of a dose of the drug exceeding the dispensable quantity of the drug still held in the cartridge. The drug delivery device may be a pen-type device. The drug delivery device may be an injection device, in particular a pen-type injector.

According to an embodiment, the stop member comprises a resilient member. The stop member may comprise a resiliently mounted member. The interaction member may comprise at least one cavity.

Preferably, the stop member and the interaction member comprise a dimension suitable to cooperate, in particular to couple, with one another in the locking mode. The stop member and the interaction member may be adapted and arranged to releasably or permanently interlock with each other in the locking mode. Accordingly, relative movement, in particular axial movement, of the drive member and the piston rod may be prevented in at least one direction in the locking mode.

According to an embodiment, if the at least one stop member is provided on the piston rod, the stop member is biased radially outwardly with respect to the housing when the assembly is in the non-locking mode. If the at least one stop member is provided on the drive member, the stop member may be biased radially inwardly with respect to the housing when the assembly is in the non-locking mode.

The stop member may be adapted to relax at least partially in the radial inward or in the radial outward direction when the assembly switches from the non-locking mode into the locking mode. When the stop member relaxes radially inwardly or radially outwardly, the stop member and the interaction member are expediently adapted and arranged to mechanically cooperate such that further movement, in particular proximal movement, of the drive member with respect to the piston rod is prevented.

According to an embodiment, the assembly comprises a dose member. In the non-locking mode, the dose member may be rotatable and/or axially displaceable in the proximal direction with respect to the housing and with respect to the piston rod for setting the dose. In the non-locking mode, the dose member may be rotatable and/or axially displaceable in the distal direction with respect to the housing and with respect to the piston rod for correcting the set dose. The drive member may be adapted and arranged to follow displacement, in particular axial displacement, of the dose member with respect to the housing and with respect to the piston rod for setting and for correcting the dose.

According to an embodiment, the dose member is rotatable with respect to the housing. The dose member and the drive member may be adapted to be releasably coupled to one another preferably via a clutch connection. When the dose member and the drive member are decoupled, the dose member may be rotatable with respect to the drive member, e.g. when setting and/or correcting the dose. When the dose member and the drive member are coupled, rotational movement of the dose member may be converted into rotational movement of the drive member with respect to the housing, e.g. when delivering the set and/or corrected dose.

As described later on in more detail in connection with the exemplary embodiments, the device may, according to an embodiment, comprise a clicker assembly. The clicker assembly may comprise a first clicker means. The first clicker means may be coupled, preferably splined, to the dose member. The clicker assembly may comprise a second clicker means. The clicker assembly may comprise a third clicker means. The first clicker means and the second clicker means may be configured to rotate with respect to the third clicker means when the dose member is rotated in a first rotational direction, e.g. for setting a dose of a drug. The first clicker means may be configured to rotate with respect to the second and to the third clicker means when the dose member is rotated in a second rotational direction, e.g. for correcting and/or delivering the dose. The second rotational direction may be opposite to the first rotational direction.

According to an embodiment, a spring member is provided. The spring member may be adapted and arranged to keep the drive member and the dose member decoupled to permit relative rotational movement of the dose member and the drive member, e.g. when setting or correcting the dose.

According to an embodiment, the piston rod is splined to the drive member.

According to an embodiment, the piston rod comprises at least one thread. The thread may be flattened in at least one axially extending portion. The drive member may comprise at least one flattened portion. This flattened portion may extend axially along the inner surface of the drive member. The piston rod may be splined to the drive member, e.g. by mechanical cooperation of the flattened inner portion and the flattened axially extending thread portion.

Accordingly, the piston rod may be adapted to follow rotational movement of the drive member when delivering the set dose. The drive member may be axially displaceable with respect to the piston rod when setting and/or correcting the dose. This may help to further increase dose accuracy.

According to an embodiment, in the locking mode, a dose setting action of the assembly is prevented due to mechanical cooperation of the stop member and the interaction member. In the locking mode, the piston rod and the drive member may be releasably axially interlocked by mechanical cooperation of the interaction member and the stop member. In this context, the term "releasably" preferably means that relative movement of the drive member and the piston rod in at least one direction, in particular an axial direction, may be enabled in the locking mode. Accordingly, a dose correction action of the assembly may be enabled in the locking mode.

In case the dose was not set correctly, the user may thus be able to correct the set dose even starting from the locking mode. In this way, provision of a user-friendly drug delivery device is facilitated.

According to an embodiment, the interaction member comprises an oblique side face. The oblique side face is expediently arranged in a proximal end section, preferably at a proximal end-face, of the interaction member. The oblique side face may be adapted and arranged to allow movement of the drive member in the distal direction with respect to the piston rod for correcting the set dose in the locking mode.

Preferably, a distal-end face of the interaction member is more radially oriented than the proximal, in particular the oblique, end-face of the interaction member.

According to an embodiment, when the drive member is moved in the distal direction with respect to the piston rod for correcting the set dose starting from the locking mode, the assembly is configured to be switched from the locking mode back into the non-locking mode.

Accordingly, setting and dispensing of a subsequent dose may be enabled after the dose was corrected in the locking mode.

According to an embodiment, in the locking mode, the piston rod and the drive member are permanently axially interlocked by mechanical cooperation of the interaction member and the stop member. Accordingly, a dose setting and/or a dose correction action may be prevented in the locking mode.

Distal movement of the drive member with respect to the piston rod may be prevented in the locking mode. Hence, in contrast to the previously described releasable interlocking of the drive member and the piston rod in the locking mode, switching of the assembly from the locking mode back into the non-locking mode may be prevented.

According to an embodiment, the assembly comprises a dose button. The dose button may be connected to the drive member. The drive member may be rotatably connected to the dose button such that the drive member may rotate with respect to the dose button in at least one direction or in two directions. The dose button may be secured to the drive member against axial movement with respect to the drive member. The drive member and the dose button may be adapted to be coupled to one another by a uni-directional rotational coupling. The uni-directional rotational coupling may be configured to permit rotational movement of the drive member with respect to the dose button in one rotational direction, in particular when delivering the set dose. The uni-directional rotational coupling may be configured to prevent rotational movement of the drive member with respect to the dose button in the opposite rotational direction, e.g. when resetting the device.

Accordingly, during a dose delivery action, the dose button is prevented from rotating with respect to the housing. This may help to facilitate provision of a user-friendly drug delivery device.

According to an embodiment, the dose button is configured to be pushed for delivering the set dose. The dose button may be displaced in the distal direction with respect to the dose member for coupling the dose member and the drive member by the clutch connection. This movement of the dose button may carry the drive member with the dose button in the distal direction, thereby closing the clutch connection.

After having coupled the dose member and the drive member, the drive member follows rotation of the dose member with respect to the housing. Accordingly, the drive member may be enabled to drive rotation of the piston rod for dispensing the dose.

According to a preferred embodiment an assembly for a drug delivery device is provided, comprising:
a housing having a distal end and a proximal end,
a piston rod,
a drive member, the drive member being moveable in a proximal direction with respect to the housing and with respect to the piston rod for setting a dose of a drug,
at least one stop member which is provided on one of the piston rod and the drive member and which is radially moveable with respect to the one of the piston rod and the drive member on which it is provided,
at least one interaction member which is provided on the other one of the piston rod and the drive member.

In a non-locking mode of the assembly, the stop member is radially biased, and the stop member and the interaction member are arranged axially spaced apart from each other by an axial distance, the axial distance being reduced by a dosing distance when the drive member is moved in the proximal direction. When the dosing distance corresponds to the axial distance, the assembly is configured to switch into a locking mode. For switching into the locking mode, the radial bias of the stop member is permitted to decrease at least partially to bring the stop member and the interaction member in mechanical cooperation. When the stop member and the interaction member mechanically cooperate, the stop member and the interaction member are configured to axially interlock the piston rod and the drive member such that, in the locking mode, movement of the drive member in the proximal direction with respect to the piston rod is prevented.

The interaction member and the stop member and, in particular mechanical cooperation of the interaction member and the stop member, may provide an end-stop mechanism for the drug delivery device. Setting of a dose of the drug exceeding a quantity of the drug still held in the device is thus effectively prevented. In this way, underdosing, which may have fatal or even lethal consequences for the user, may be prevented.

According to a further preferred embodiment a piston rod for a drug delivery device is provided, comprising a resiliently mounted member arranged in a proximal end section of the piston rod, the resiliently mounted member being radially moveable with respect to the piston rod.

This piston rod may be especially suited to be integrated in a drug delivery device for providing the previously mentioned end-stop mechanism.

Of course, features described above in connection with different aspects and embodiments may be combined with each other and with features described below.

Further features, advantages and refinements become apparent from the following description of the exemplary embodiments in connection with the accompanying figures.

BRIEF DESCRIPTION OF THE DRAWINGS

Like elements, elements of the same kind and identically acting elements may be provided with the same reference numerals in the figures.

DETAILED DESCRIPTION

An exemplary drug delivery device is described in connection with the FIGS. 1 to 13.

Figure 1:
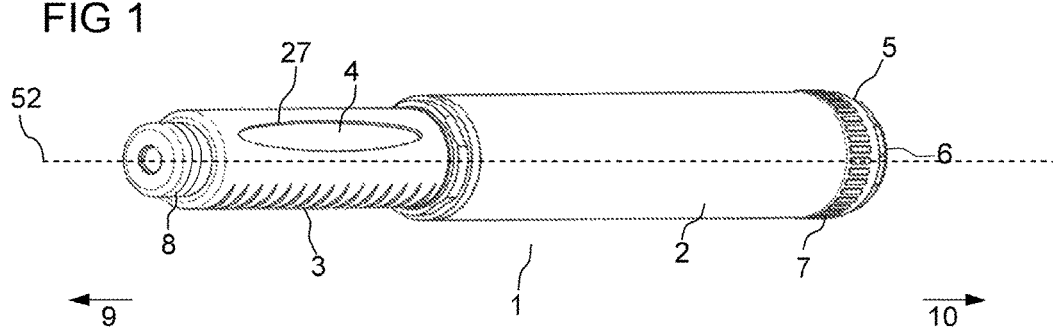
FIG. 1 schematically shows a perspective view of an exemplary embodiment of a drug delivery device, FIG. 2 schematically shows a perspective view of parts of the drug delivery device of FIG. 1, FIG. 3 schematically shows a sectional view of the drug delivery device of FIG. 1, FIG. 4 schematically shows a sectional view of parts of the drug delivery device of FIG. 1, FIG. 5 schematically shows a partly sectional side view of other parts of the drug delivery device of FIG. 1, FIG. 6 schematically shows a partly sectional side view of parts of the drug delivery device of FIG. 1, FIG. 7 schematically shows a sectional view of the drug delivery device of FIG. 1 during dose setting, FIGS. 8A and 8B schematically show a partly sectional view of parts of the drug delivery device of FIG. 7 during dose setting, FIGS. 9A and 9B schematically show a sectional view of the parts of the drug delivery device of FIG. 7 during dose dispensing, FIG. 10 schematically shows a sectional view of the drug delivery device of FIG. 1 after having set a last dose, FIG. 11 schematically shows a sectional view of a part of the drug delivery device of FIG. 10, FIG. 12 schematically shows a sectional view of the drug delivery device of FIG. 10 after having dispensed the last dose, FIGS. 13A and 13B schematically show a perspective sectional view of parts of the drug delivery device of FIG. 1.

In FIG. 1, a drug delivery device 1 is shown. The drug delivery device 1 comprises a housing 2. The drug delivery device 1 and the housing 2 have a distal end and a proximal end. The term "distal end" designates that end of the drug delivery device 1 or a component thereof which is or is to be arranged closest to a dispensing end of the drug delivery device 1. The distal end of the device 1 is indicated by arrow 9. The term "proximal end" designates that end of the device 1 or a component thereof which is or is to be arranged furthest away from the dispensing end of the device 1. The proximal end of the device 1 is indicated by arrow 10.

The drug delivery device 1 comprises a cartridge holder 3. The cartridge holder 3 is, preferably releasably, secured to the housing 2, e.g. by mechanical cooperation of a thread 28 (see FIG. 2) of the cartridge holder 3 and a mating thread arranged at an inner surface of the housing 2 (not explicitly shown).

The drug delivery device 1 comprises a cartridge 4. The cartridge 4 is retained in the cartridge holder 3. The cartridge holder 3 stabilizes the cartridge 4 mechanically. The cartridge holder 3 comprises a window aperture 27. The window aperture 27 enables a user to view the cartridge 4, e.g. the fill level of the cartridge 4 and/or symbols relating to a dosage scale provided on the cartridge 4, through the cartridge holder 3.

Figure 3:
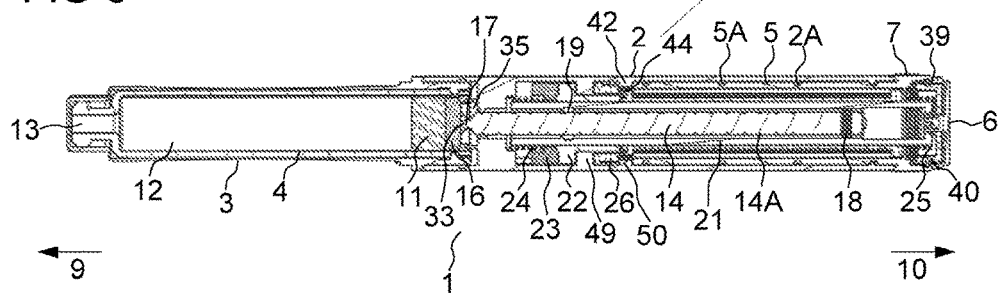

The cartridge 4 may hold a plurality of doses of a drug 12 (see FIG. 3). The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound.

In a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis.

In a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The cartridge 4 has an outlet 13 (see FIG. 3). The drug 12 can be dispensed from the cartridge 4 through the outlet 13 (see FIG. 3). The outlet 13 may be covered by a membrane. The membrane may protect the drug 12 against external influences during storage of the cartridge 4.

The drug delivery device 1 may comprise a needle assembly (not explicitly shown), comprising a needle. The needle assembly may be releasably attached to the cartridge holder 3, for example by means of an engaging means 8 (see FIGS. 1 and 2), e.g. a thread. The membrane may be pierced by the needle for dispensing a dose of the drug 12 from the cartridge 4. Alternatively, the drug delivery device 1 may be a needle-free device.

The drug delivery device 1 comprises a bung 11 (see FIG. 3). The bung 11 is moveably retained in the cartridge 4. The bung 11 seals the cartridge 4 proximally. Movement of the bung 11 in the distal direction with respect to the cartridge 4 causes the drug 12 to be dispensed from the cartridge 4 through the outlet 13, provided that fluid communication was established between the interior and the exterior of the cartridge 4, e.g. the membrane was pierced by the needle.

The drug delivery device 1 may be an injection device. The drug delivery device 1 may be a pen-type device, in particular a pen-type injector. The device 1 may be a disposable or a re-usable device. Preferably, the device 1 is configured to dispense variable doses, in particular user-settable doses, of the drug 12. Alternatively, the device 1 may be configured to dispense fixed doses of the drug 12, in particular pre-set doses which may not be varied by the user. The drug delivery device 1 may be a manually, in particular a non-electrically, driven device.

Figure 4:
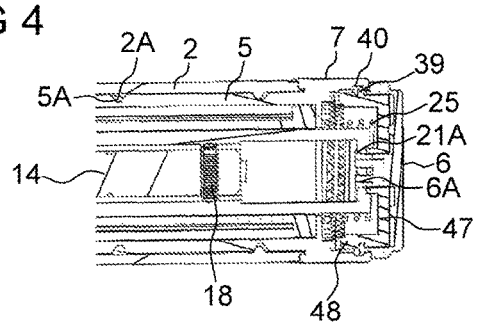
Figure 6:
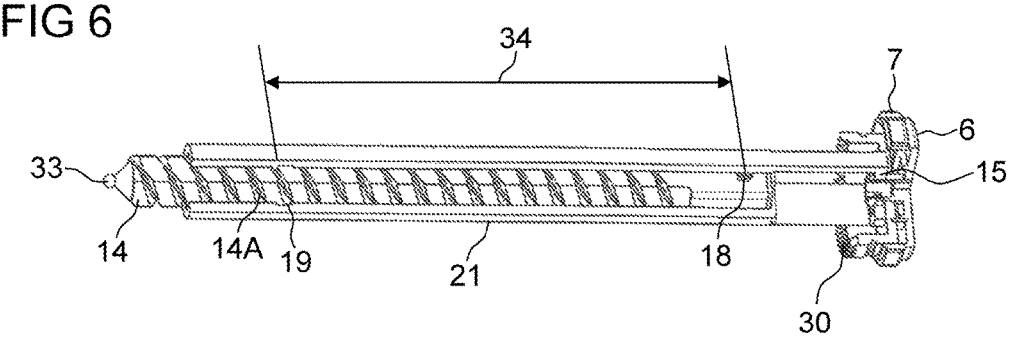

The drug delivery device 1 comprises a piston rod 14 (see FIGS. 3 and 4 and, in particular, FIG. 6). The piston rod 14 operates through the housing 2 of the drug delivery device 1. The piston rod 14 is designed to transfer force to the bung 11, thereby driving the bung 11 in the distal direction with respect to the cartridge 4 and the housing 2. In this way, a dose of the drug 12 is dispensed from the cartridge 4 provided that the outlet 13 was opened, e.g. the membrane was pierced by the needle as described above. The size of the dispensed dose is determined by the distance by which the bung 11 is displaced in the distal direction with respect to the housing 2.

A bearing member 16 (see FIG. 3) is arranged between the bung 11 and the piston rod 14 to advance the bung 11. The bearing member 16 is displaceable together with the piston rod 14 with respect to the housing 2. The piston rod 14 is preferably rotatable with respect to the bearing member 16. The bearing member 16 is axially locked to the piston rod 14, for example by mechanical cooperation of an engaging means 33, e.g. a protrusion, of the piston rod 14 and a mating engaging means 17, e.g. an indentation, of the bearing member 16. Preferably, the bearing member 16 is snap-fitted to the piston rod 14.

Figure 2:
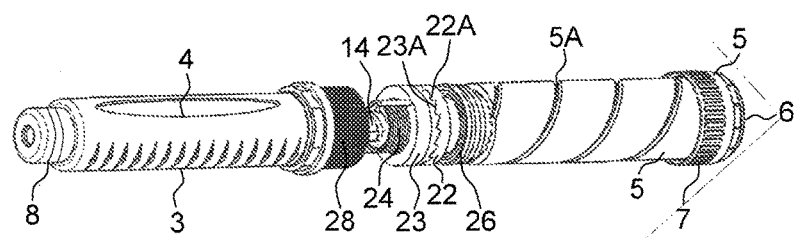

The drug delivery device 1 comprises a drive mechanism. The drive mechanism comprises a dose member 5 (see in particular FIGS. 2 and 5). The dose member 5 may comprise or may be embodied as a sleeve. The dose member 5 is rotatable with respect to the housing 2 for setting, correcting and/or for delivering the dose as described later on in more detail. The dose member 5 comprises an outer thread 5A, as shown in FIGS. 2 and 3, for example. The housing 2 comprises a mating inner thread 2A (see FIG. 3). Rotation of the dose member 5 with respect to the housing 2 is, thus, on account of the cooperating threads 5A and 2A converted into axial movement of the dose member 5 with respect to the housing 2 by mechanical cooperation of outer thread 5A and inner thread 2A.

The dose member 5 is rotatable in a first rotational direction with respect to the housing 2 for setting a dose of the drug 12. The first rotational direction is clockwise, for example. The dose member 5 is rotatable in a second rotational direction with respect to the housing 2 for correcting and/or delivering the set dose of the drug 12. The second rotational direction is opposite to the first rotational direction. The second rotational direction is counter-clockwise, for example. The dose member 5 comprises a dose setting grip 7. The dose setting grip 7 can be gripped by a user for rotating the dose member 5 for setting and/or correcting the dose.

A, preferably user-applied, force or torque causing the dose member 5 to be rotated in the second rotational direction is transferred to the piston rod 14 for delivering the set and/or corrected dose. Preferably, when setting and/or correcting the dose, the drive mechanism is configured to leave the piston rod 14 stationary with respect to the housing 2. Operation of setting, correcting and delivering the dose will be described in connection with FIGS. 7 to 12.

The drive mechanism comprises a drive member 21 (see, for example, FIG. 3). The drive member 21 may comprise or may be embodied as a sleeve. The drive member 21 is axially and, in a limited fashion, rotationally moveable with respect to the housing 2, which is explained later on in more detail.

The drive mechanism comprises a dose button 6. The dose button 6 is configured to be pushed by a user for dispensing the set and/or corrected dose. The dose button 6 is, preferably releasably, secured to the drive member 21. The dose button 6 may be retained in the drive member 21. The dose button 6 comprises an engaging means 6A (see FIG. 4), for example a protrusion. The protrusion may protrude from the dose button 6, in particular from the middle of the dose button 6, in the distal direction with respect to the drive member 21. The drive member 21 comprises a mating engaging means 21A (see FIG. 4), for example an indentation. The indentation may be arranged at a proximal end face, in particular in the middle of the proximal end face, of the drive member 21. Due to mechanical cooperation of engaging means 6A and mating engaging means 21A the dose button 6 is secured against axial movement with respect to the drive member 21. Relative rotational movement between drive member 21 and dose button 6 is, however, allowed.

Figure 13A:
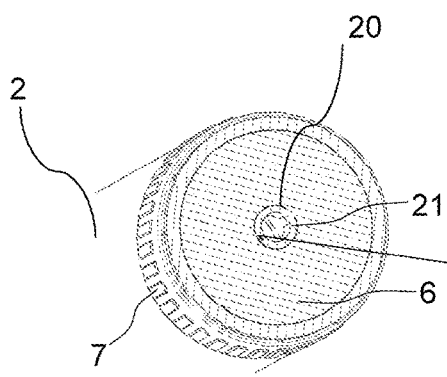
Figure 13B:
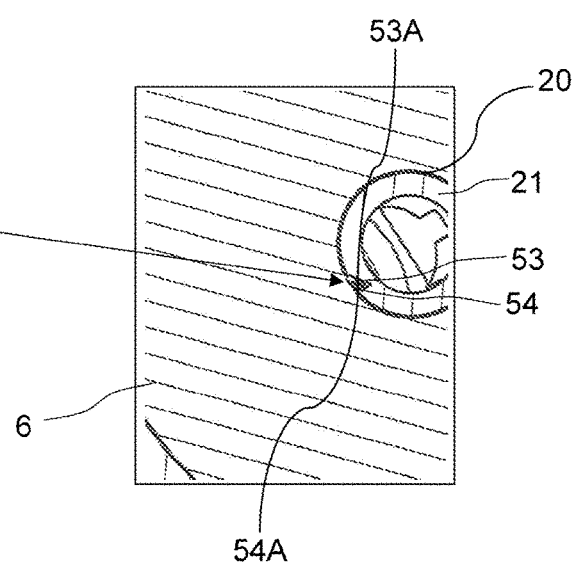

The dose button 6 is preferably uni-directionally rotationally coupled to the drive member 21. The drive member 21 comprises an engaging means 53 (see FIGS. 13A and 13B). Engaging means 53 may be an indentation. Engaging means 53 may comprise an oblique side face 53A and a steep side face. Engaging means 53 is arranged at the proximal end face, in particular in the middle of the proximal end face, of the drive member 21. The dose button 6 comprises a mating engaging means 54 (see FIGS. 13A and 13B). Mating engaging means 54 may be a lug protruding radially inwardly from the dose button 6, in particular from a circular recess 20 arranged in the middle of the dose button 6, as shown in FIGS. 13A and 13B. Mating engaging means 54 may be a resilient member. Mating engaging means 54 may be resilient in the radial direction with respect to the housing 2. Mating engaging means 54 may comprise an oblique side face 54A and a steep side face.

The dose button 6 follows rotation of the drive member 21 when the drive member is rotated in the first rotational direction, e.g. for resetting the device 1 after having introduced a replacement cartridge into the device 1 which is described later on in more detail. Mechanical cooperation of oblique side face 53A and oblique side face 54A enables rotation of the drive member 21 with respect to the dose button 6 when the drive member 21 is rotated in the second rotational direction with respect to the housing 2, e.g. for delivering the dose. In particular, for delivering the dose, the oblique side faces 53A and 54A mechanically cooperate, in particular slide along each other, to allow rotation of the drive member 21 with respect to the dose button 6 for delivering the dose. Mechanical cooperation of the steep side faces, however, prevent rotation of the drive member 21 with respect to the dose button 6, e.g. for resetting the device 1. Accordingly, due to mechanical cooperation of engaging means 53 and mating engaging means 54 the dose button 6 is thus uni-directionally rotationally locked to the drive member 21.

The drive member 21 is preferably arranged within the dose member 5. The drive member 21 may be, preferably permanently, secured against axial displacement with respect to the dose member 5. The drive member 21 comprises an engaging means 39 (see FIGS. 3 and 4). Engaging means 39 is arranged at the proximal end section of the drive member 21. Engaging means 39 protrudes radially outwardly from the drive member 21. Engaging means 39 is arranged around the perimeter of the drive member 21. Preferably, engaging means 39 is a flange.

The dose member 5 comprises a mating engaging means 40 (see FIGS. 3 and 4). Mating engaging means 40 is adapted and arranged to mate with engaging means 39. Engaging means 40 is provided on an inner surface of the dose member 5. Engaging means 40 is arranged along the inner surface of the dose member 5. Preferably, engaging means 40 is a guide notch. By means of mechanical cooperation of engaging means 39 and mating engaging means 40, the drive member 21 is secured against major axial displacement with respect to the dose member 5, in particular for setting and/or correcting the dose. Engaging means 40 expediently comprises an axial dimension greater than the axial dimension of engaging means 39. The axial dimension of engaging means 40 may be such that the drive member 21 can be slightly axially moved with respect to the dose member 5 when the dose button 6 is pushed for dispensing the set dose, which is explained later on in more detail. Engaging means 39 and mating engaging means 40 are adapted to prevent proximal movement of the dose member 5 with respect to the drive member 21 with rotational movement of the dose member 5 with respect to the drive member 21 being allowed.

The drive member 21 is, preferably releasably, rotationally coupled to the dose member 5 by means of a clutch connection. The clutch connection is expediently closed during dose delivery. Accordingly, the closed clutch connection prevents rotational movement of the dose member 5 with respect to the drive member 21, when the dose member 5 is rotated in the second rotational direction with respect to the housing 2 for delivering the dose.

Figure 8A:
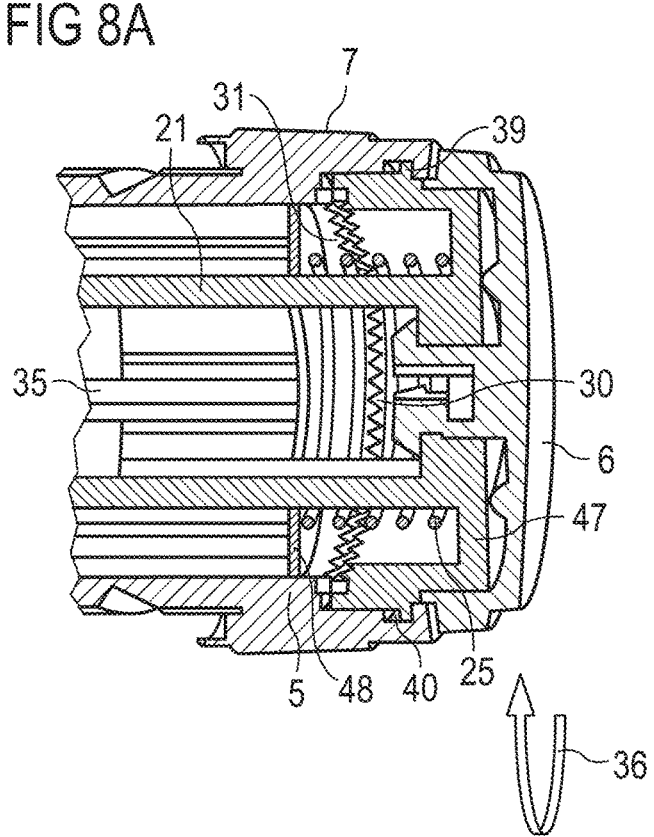

The drive member 21 comprises a plurality of teeth 30 (see FIG. 8A). Teeth 30 are arranged at the proximal end section of the drive member 21. Teeth 30 may be disposed along a perimeter of drive member 21. The dose member 5 comprises a plurality of teeth 31 (see FIG. 8A). Teeth 31 are arranged at the proximal end section of the dose member 5. Teeth 31 are disposed along a perimeter of dose member 5.

Teeth 30 and teeth 31 extend along the rotation axis. The rotation axis may be oriented along the main longitudinal axis 52 (see FIG. 1) of the housing 2. Preferably, the rotation axis runs along the piston rod 14 and, in particular, along a main direction of extent of the piston rod 14. Teeth 30 and teeth 31 are configured to mate, in particular to engage, with each other. Due to mechanical cooperation of teeth 30 and teeth 31, the drive member 21 is rotationally locked to the dose member 5 such that no relative rotation between the dose member 5 and the drive member 21 is allowed when the teeth 30 and 31 are engaged.

As shown in FIG. 8A, a spring member 25 is arranged between the drive member 21 and the dose member 5. Spring member 25 is arranged around the proximal end section of the drive member 21. In particular, the spring member 25 is arranged between a radially outwardly protruding shoulder or flange portion 47 (see FIGS. 4 and 8A) of the drive member 21 and a radially inwardly protruding shoulder or flange portion 48 (see FIG. 4 and, in particular, FIG. 8A) of the dose member 5. The spring member 25 may bear on the respective shoulder or flange portion 47, 48. The spring member 25 may comprise a pressure spring. The spring member 25 may be or may comprise a coil spring, preferably a helical coil spring. During dose delivery, the spring member 25 is in a compressed, in particular in an axially biased, state. During dose setting, the spring member 25 may be arranged to keep the clutch connection open.

For delivering the dose, the dose button 6 and, thus, the drive member 21, are pushed slightly distally with respect to the housing 2 and with respect to the dose member 5. Thereby, the spring member 25 is compressed, in particular pushed against the shoulder or flange portion 48 of the dose member 5. Accordingly, teeth 30 and teeth 31 are brought into engagement for rotationally locking the drive member 21 and the dose member 5.

The distal movement of the drive member 21 with respect to the dose member 5 for closing the clutch connection may be larger than the axial dimension, in particular the depth, of a respective tooth 30, 31. The distal movement of the drive member 21 with respect to the dose member 5 is determined by the axial dimension of engaging means 40, e.g. the guide notch, of the dose member 5. Consequently, the axial dimension of engaging means 40 may be at least equal to, preferably greater than, the depth of a respective tooth 30, 31.

After having delivered the dose and, in particular, for setting a subsequent dose the dose button 6 is released. Accordingly, the spring member 25 relaxes axially, in particular proximally, with respect to the housing 2. Thereby, the spring member 25 pushes the drive member 21 back in the proximal direction with respect to the dose member 5. Thus, teeth 30 and teeth 31 are brought out of engagement. Accordingly, for setting and/or correcting the dose, the clutch connection is opened. Hence, when setting and/or correcting the dose, the drive member 21 is prevented from following rotation of the dose member 5 in the first and/or in the second rotational direction for setting and/or for correcting the dose. When setting and/or correcting the dose, rotation of the dose member 5 is converted into axial movement of the drive member 21 with respect to the housing 2 due to mechanical cooperation of engaging means 39 and mating engaging means 40. The drive member 21 is prevented from slight axial, in particular distal, movement with respect to the dose member 5 and hence, from an unintentional dose delivery action, by means of the spring member 25.

The drive member 21 is splined to the piston rod 14. The piston rod 14 comprises an outer thread 14A. Preferably, the outer thread 14A is flattened in an axially extending portion. The drive member 21 comprises a flattened portion arranged along an inner surface of the drive member 21. Preferably, the piston rod 14 is splined to the drive member 21 by mechanical cooperation of the flattened inner portion and the flattened outer thread 14A. The splined connection of drive member 21 and the piston rod 14 prevents rotational movement of the drive member 21 with respect to piston rod 14 and vice versa. Hence, the drive member 21 and the piston rod 14 may be permanently rotationally locked. However, the piston rod 14 and the drive member 21 are axially displaceable with respect to each other. In particular, the drive member 21 is axially displaceable with respect to the piston rod 14 for setting and/or correcting a dose of the drug 12. The piston rod 14 is displaceable with respect to the drive member 21 when delivering the set dose.

The drive member 21 is configured to transfer force, preferably torque, to the piston rod 14. The transferred force causes the piston rod 14 to be rotated with respect to the housing 2 for delivering the dose.

Additionally or alternatively, the transferred force causes the piston rod 14 to be displaced in the distal direction with respect to the housing 2 for delivering the set dose of the drug 12. In particular, a counterpart to outer thread 14A, e.g. a further thread (not explicitly shown), may be provided inside housing 2 for a threaded engagement of the housing 2 and piston rod 14. Rotational movement of the piston rod 14 is thus converted into axial movement of the piston rod 14 in the distal direction with respect to the housing 2 due to the threaded engagement of the piston rod 14 and the housing 2.

As, when setting and/or correcting the dose, rotation of the drive member 21 with respect to the housing 2 is prevented, movement of the piston rod 14 with respect to the housing 2 is prevented as well when setting and/or correcting the dose. This may help to increase dose accuracy.

The drug delivery device 1 comprises a clicker assembly. The clicker assembly comprises a first clicker means 26. The drug delivery device 1 comprises a second clicker means 22. The drug delivery device 1 comprises a third clicker means 23.

The clicker means 22, 23, 26 (see in particular FIGS. 3 and 5) may comprise or may be embodied as a sleeve, respectively. The first clicker means 26 is rotationally locked to the dose member 5. Preferably, the first clicker means 26 is splined to the dose member 5, for example by means of mechanical cooperation of a guide nut 35 (see FIG. 8A) arranged axially along an inner surface of the dose member 5 and a corresponding guide rib (not explicitly shown) arranged axially along an outer surface of the first clicker means 26. The first clicker means 26 is secured against axial displacement with respect to the housing 2, for example by means of protruding portions 49 and 50 (see FIG. 3).

Figure 5:
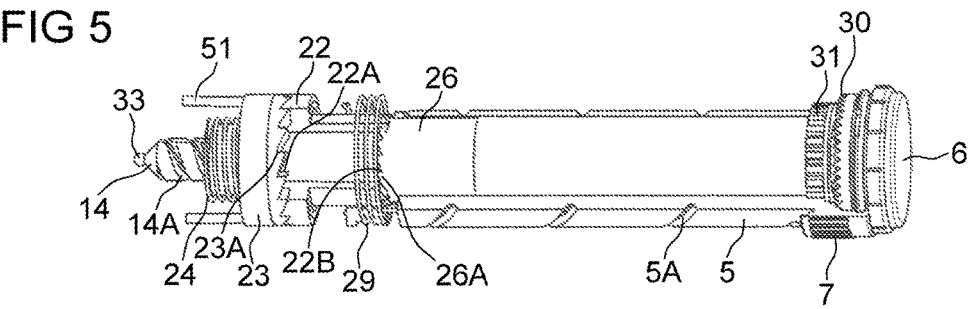

The device 1 comprises a spring member 29 (see FIG. 5). Spring member 29 may comprise a coil spring like a helical coil spring, for example. Spring member 29 may be arranged at least partly around the first clicker means 26. The spring member 29 may help preventing the first clicker means 26 from axial movement with respect to the housing 2.

The second clicker means 22 is rotatable with respect to the housing 2. The second clicker means 22 is arranged to abut and/or engage the first clicker means 26. Rotational movement of the first clicker means 26 with respect to the second clicker means 22 may be prevented when the dose member 5 and, hence, the first clicker means 26 is rotated in the first rotational direction with respect to the housing 2, e.g. for setting the dose. Rotational movement of the first clicker means 26 with respect to the second clicker means 22 may be enabled when the dose member 5 and, hence, the first clicker means 26 is rotated in the second rotational direction with respect to the housing 2, e.g. for correcting and/or delivering the dose.

The second clicker means 22 comprises a toothing having a plurality of teeth 22B (see FIG. 5). The first clicker means 26 comprises a toothing having a plurality of teeth 26A. Teeth 22B and teeth 26A are configured to mate with each other. Mechanical cooperation of the teeth 22B, 26A enables common rotation of the clicker means 26, 22 in the first rotational direction for setting the dose. A respective tooth of teeth 22B and teeth 26A is ramp-shaped, hence enabling rotational movement of the first clicker means 26 in the second rotational direction with respect to the second clicker means 22. In particular, when the dose member 5 and, hence, the first clicker means 26 is rotated in the second rotational direction with respect to the housing 2, e.g. for delivering the dose, teeth 26A of the first clicker means 26 slide along teeth 22B and, hence, the first clicker means 26 rotates with respect to the second clicker means 22.

The second clicker means 22 is arranged between the third clicker means 23 and the first clicker means 26. The third clicker means 23 is configured to prevent rotational movement of the second clicker means 22 in the second rotational direction with respect to the housing 2 when the dose member 5 and, hence, the first clicker means 26 is rotated in the second rotational direction. The third clicker means 23 is preferably secured against rotation with respect to the housing 2.

The third clicker means 23 is arranged to abut or engage the second clicker means 22, preferably during dose setting, correction and/or delivery. The third clicker means 23 comprises a toothing having a plurality of teeth 23A. The second clicker means 22 comprises a further toothing having a plurality of teeth 22A. Teeth 23A and teeth 22A are configured to cooperate for preventing rotation of the second clicker means 22 with respect to the housing 2 and with respect to the third clicker means 23 for correcting and/or delivering the dose and for permitting rotation of the second clicker means 22 with respect to the third clicker means 23 for setting the dose.

Figure 8B:
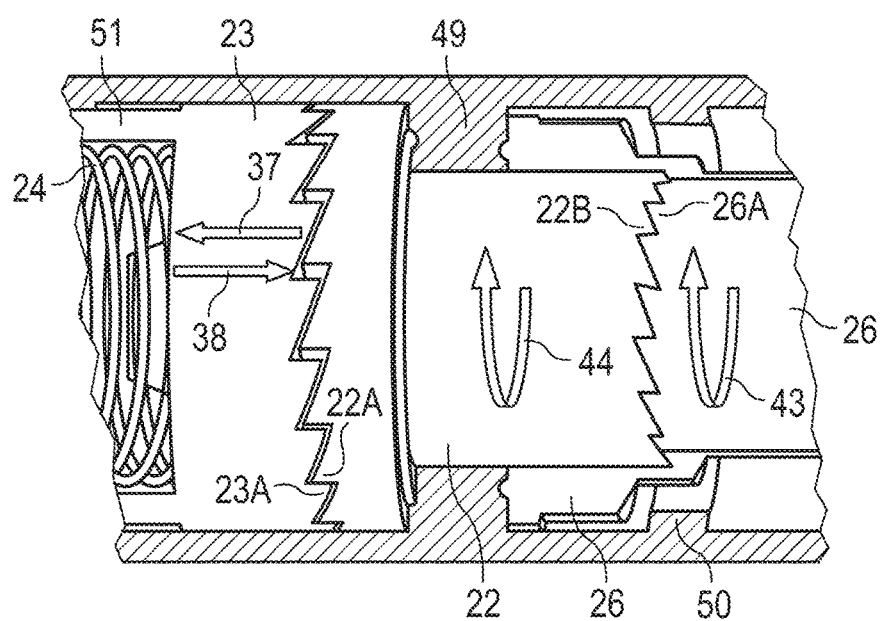
Figure 9A:
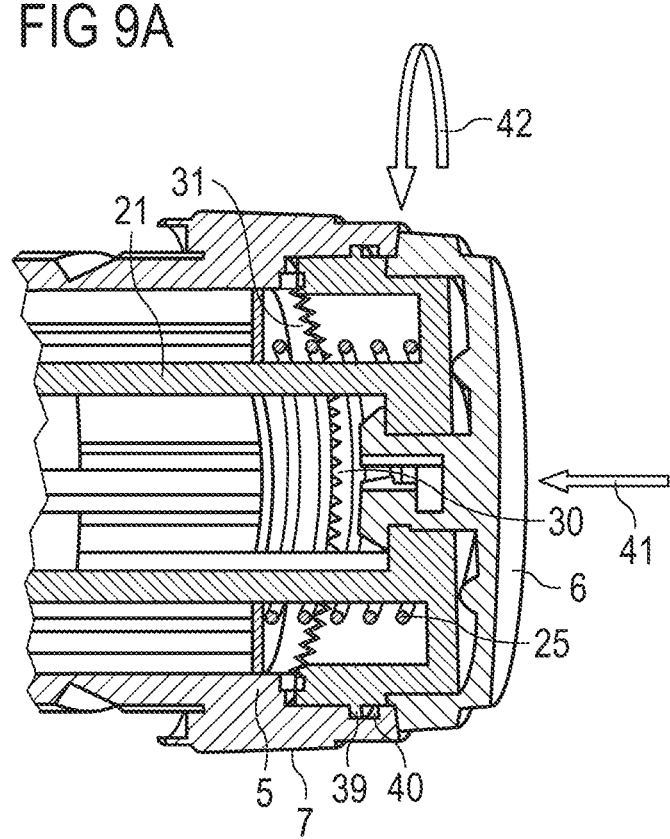
Figure 9B:
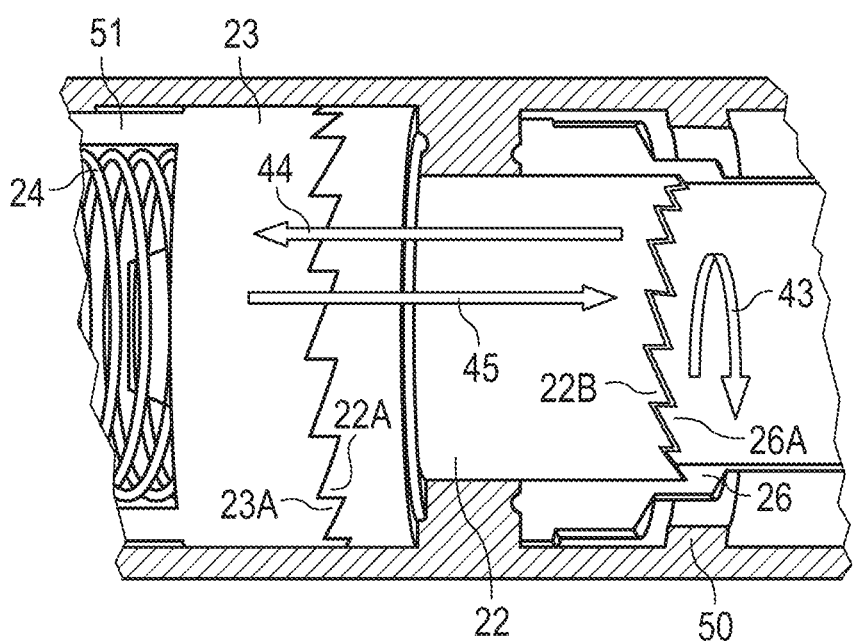

The third clicker means 23 and the second clicker means 22 are axially displaceable with respect to the housing 2, as indicated by arrows 37, 38, 44 and 45 in FIGS. 8B and 9B. The third clicker means 23 comprises one or a plurality of guiding members, for example guide lugs 51, as shown in FIG. 5. Guide lugs 51 engage with corresponding guide slots (not explicitly shown). Guide slots extend axially with respect to the housing 2. The guide slots may be provided in the housing 2.

A guide lug 51 cooperates with a guide slot to prevent rotational movement of the third clicker means 23 with respect to the housing 2 with axial movement of the third clicker means 23 and, hence, of the second clicker means 22, with respect to the housing 2 being allowed. The distance by which the second clicker means 22 and/or the third clicker means 23 may be axially displaceable with respect to the housing 2 corresponds to the maximum depth of a tooth 22B and/or 23A of the respective toothing of the second clicker means 22 and/or the third clicker means 23. Alternatively, the distance may be greater than the maximum depth of a tooth 22B and/or 23A of the respective toothing.

The drug delivery device 1 further comprises a resilient member 24, for example a spring (see FIGS. 3 and 5). The resilient member 24 may be biased. Preferably, the resilient member 24 is biased in the axial direction with respect to the housing 2. The resilient member 24 provides a force keeping the second clicker means 22 in permanent mechanical cooperation, e.g. engagement, with the third clicker means 23 and the first clicker means 26. Preferably, the force is exerted along the rotation axis.

When the second clicker means 22 and/or the third clicker means 23 are displaced in the axial, in particular in the distal, direction with respect to the housing 2, force must be applied against the force exerted by the resilient member 24. The respective clicker means 22, 23 is automatically displaced in the opposite, in particular in the proximal, direction with respect to the housing 2 by the energy stored in the resilient member 24 while displacing the second clicker means 22 and/or the third clicker means 23 distally.

The device 1 comprises the protruding portion 50 as described above. The first clicker means 26 extends through an opening in protruding portion 50. Protruding portion 50 provides a counter force to the force exerted by the resilient member 24.

The piston rod 14 is arranged and/or driven through at least one, or more, or all of the first clicker means 26, the second clicker means 22, the third clicker means 23, the drive member 21 and the dose member 5.

FIG. 6 schematically shows a partly sectional side view of another part of the drug delivery device of FIG. 1.

In particular, FIG. 6 shows the piston rod 14 and a part of the drive member 21. The device 1 comprises a stop member 18. Alternatively, the device 1 comprises two or more stop members 18. The respective stop member 18 is provided at the piston rod 14. The stop members 18 are preferably equally built. The two stop members 18 may be arranged oppositely.

Stop member 18 may be a resilient member or a member resiliently mounted on the piston rod 14. In particular, the stop member 18 may be an elastically deformable and/or deflectable member. Stop member 18 may be mounted to the piston rod 14 via at least one pressure spring, for example. In a non-locking mode of the device 1, e.g. when the amount of drug 12 still present in the cartridge 4 is great enough to set and dispense at least one subsequent maximum dose of the drug 12, the stop member 18 is biased in the radial direction, preferably the radial outward direction, with respect to the housing 2.

Preferably, the stop member 18 is connected to or is part of the piston rod 14. Alternatively, the stop member 18 may be connected to or may be part of the drive member 21 (not explicitly shown). In this case, in the non-locking mode, the stop member 18 may be biased in the radial inward direction with respect to the housing 2.

According to the embodiment shown in the figures, the stop member 18 is arranged in, preferably connected to, the proximal end section of the piston rod 14. The stop member 18 is secured against axial and rotational displacement with respect to the piston rod 14. In a locking mode of the device 1, e.g. when the maximum settable dose exceeds the quantity of drug still available in the device 1, the radial bias of the stop member 18 is at least partially reduced. The maximum settable dose is determined by the maximum distance the dose member 5 is displaceable in the proximal direction with respect to the housing 2 for setting the dose.

In the locking mode, the stop member 18 protrudes radially outwardly from the piston rod 14 further than in the non-locking mode. This is described later on in more detail. In the locking mode, the stop member 18 is adapted to mechanically cooperate with at least a part of the drive member 21 or with a member connected to the drive member 21 to prevent relative axial movement of the drive member 21 with respect to the piston rod 14 at least in one direction.

The device 1 comprises at least one interaction member 19. Alternatively, the device 1 comprises two or more interaction members 19. The interaction members 19 are preferably equally built. The two interaction members 19 may be arranged oppositely.

Preferably, the interaction member 19 is part of the drive member 21. The interaction member 19 and the drive member 21 are preferably formed unitarily. Alternatively, in case the stop member 18 is connected to or is part of the drive member 21, the interaction member 19 may be part of the piston rod 14 (not explicitly shown).

According to the embodiment shown in the figures, the respective interaction member 19 is part of the drive member 21. Preferably, the interaction member 19 is arranged in the distal end section of the drive member 21. The interaction member 19 is arranged at an inner surface of the drive member 21. The interaction member 19 may comprise a cavity, in particular an indentation, a notch or a step, for example. The cavity may be arranged circumferentially around the inner surface of the interaction member 19. The interaction member 19 may be milled or moulded into the inner surface of the drive member 21, for example. The interaction member 19 may comprise a annular nut. The interaction member 19 comprises a dimension suitable to cooperate, in particular to permanently or releasably engage, with the stop member 18 in the locking mode.

In the non-locking mode, the interaction member 19 and the stop member 18 are axially moveable with respect to each other. In the non-locking mode, the interaction member 19 is arranged at an axial distance from, in particular proximally offset from, the stop member 18. Thus, in the non-locking mode, the interaction member 19 and the stop member 18 are prevented from mechanically cooperating with one another.

In the locking mode, the interaction member 19 and the stop member 18 axially overlap. In particular, in the locking mode, the interaction member 19 mechanically cooperates, in particular interlocks, with the stop member 18. Accordingly, in the locking mode, the drive member 21 permanently or releasably interlocks with the piston rod 14. Consequently, in the locking mode, the drive member 21 is no longer axially moveable with respect to the piston rod 14. Alternatively, in the locking mode, the drive member 21 may be axially moveable with respect to the piston rod 14 only in a limited fashion, e.g. in a specific direction, which is explained later on in more detail.

In an initial state of the device 1 (see in particular FIG. 3), e.g. the state of the device 1 as originally supplied from the manufacturer, in particular, before setting a first dose of the drug 12, the interaction member 19 is arranged at an axial start position with respect to the stop member 18. In particular, the interaction member 19 and the stop member 18 may be arranged at an initial, in particular maximum, axial distance from each other. The distance is indicated by double arrow 34 in FIG. 6. Accordingly, the interaction member 19 and the stop member 18 are prevented from mechanically cooperating. The device 1 is thus in the non-locking mode. When the interaction member 19 is arranged at an axial distance from the stop member 18, the drive member 21, in particular the inner surface of the drive member 21 prevents the stop member 18 from moving in the radial direction, in particular from relaxing radially outwardly.

When setting a dose of the drug 12, the drive member 21 and, hence, the interaction member 19, is displaced in the proximal direction with respect to the housing 2 and with respect to the stop member 18. Thereby, the interaction member 19 is displaced away from its axial start position by a dosing distance. The dosing distance is determined by the thread 5A of the dose member 5.

When correcting the set dose, the drive member 21 and, hence, the interaction member 19, is displaced in the distal direction with respect to the housing 2 and with respect to the stop member 18. Thereby, the interaction member 19 is displaced back towards its axial start position by a distance smaller than the dosing distance. If the dose is unset, the interaction member 19 may resume its axial start position.

When delivering the set or corrected dose, the interaction member 19 and the stop member 18 are displaced distally, respectively. Thereby, the interaction member 19 is displaced distally by the same distance, e.g. the dosing distance, it was displaced proximally with respect to the stop member 18 when setting the dose. However, the initial distance between the interaction member 19 and the stop member 18 as indicated by arrow 34 is reduced due to the distal movement of the piston rod 14 and, hence, of the stop member 18 with respect to the housing 2 during dose delivery.

When the maximum settable dose exceeds the quantity of drug still available in the device 1, e.g. in case the set dose of the drug 12 exceeds the quantity of the drug 12 present in the cartridge 4, the maximum dosing distance is greater than or equal to the axial distance between the interaction member 19 and the stop member 18. Accordingly, at the end of or during the last dose setting procedure, the stop member 18 and the interaction member 19 axially overlap. When the stop member 18 and the interaction member 19 axially overlap, the radial bias of the stop member 18 is allowed to decrease. In particular, the stop member 18 relaxes radially outwardly with respect to the housing 2 and engages the interaction member 19. Accordingly, at the end of the dose setting procedure, the interaction member 19 and the stop member 18 couple with each other. Accordingly, at the end of the last dose setting procedure, the device 1 was switched from the non-locking mode into the locking mode.

In the locking mode, a distal side face of the decompressed stop member 18 abuts a proximal side face of the interaction member 19. Due to mechanical cooperation of the stop member 18, in particular its distal side face, and the interaction member 19, in particular its proximal side face, the drive member 21 is permanently or releasably axially locked to the piston rod 14. Hence, further axial movement of the drive member 21 with respect to the piston rod 14, in particular proximal movement required for increasing the size of the dose, can be prevented due to mechanical cooperation of the interaction member 19 and the stop member 18. Underdosing, which may have fatal or even lethal consequences for the user, may be prevented.

The interaction member 19 may comprise an oblique side face (not explicitly shown). This oblique side face may be arranged in a proximal end section of the interaction member 19. In particular, the proximal side face of the interaction member 19 may comprise the oblique side face. The piston rod 14 and the drive member 21 may be releasably axially interlocked in the locking mode by mechanical cooperation of the interaction member 19, in particular the oblique side face of the interaction member 19, and the stop member 18. Consequently, distal movement of the drive member 21 with respect to the piston rod and, hence, a dose correction action may be enabled in the locking mode.

When the drive member 21 is displaced in the distal direction with respect to the piston rod 14 for correcting the set dose in the locking mode, the stop member 18 mechanically cooperates with, in particular slides along, the oblique side face of the interaction member 19. Accordingly, the stop member 18 moves radially inwardly. Hence, the device 1 is switched from the locking mode back into the non-locking mode. In the non-locking mode, further movement of the drive member 21 in the proximal direction with respect to the piston rod 14 and, in particular, a subsequent dose setting action may be enabled. When, during the subsequent dose setting action, the interaction member 19 axially overlaps with the stop member 18, the device 1 is switched again from the non-locking mode into the locking mode.

Alternatively, the interaction member 19 may be free of an oblique side face. Consequently, in the locking mode, the piston rod 14 and the drive member 21 may be permanently axially interlocked by mechanical cooperation of the interaction member 19 and the stop member 18. In this case, a dose correction action may be prevented once the device 1 was switched from the non-locking mode into the locking mode. In particular, switching of the device 1 from the locking mode back into the non-locking mode may be prevented in this way. Thus, once the last dose was set, it has to be delivered and cannot be unset.

Figure 7:
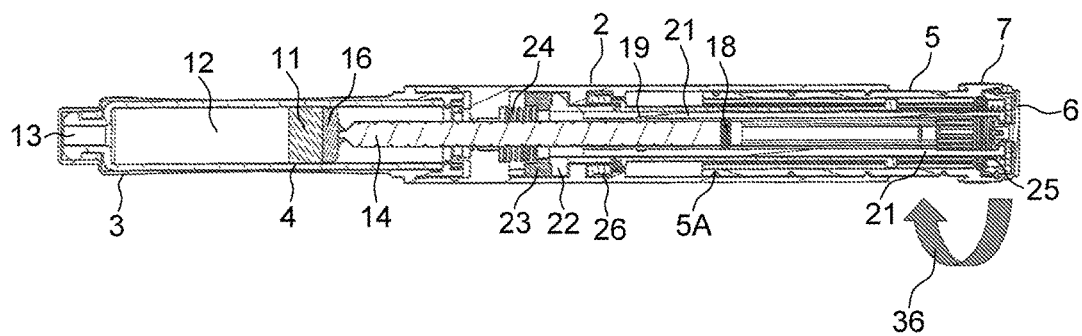

FIG. 7 schematically shows a sectional view of the drug delivery device of FIG. 1 during dose setting.

FIGS. 8A and 8B schematically show a partly sectional view of parts of the drug delivery device of FIG. 7 during dose setting.

For setting the dose, the user rotates the dose setting grip 7 and, hence, the dose member 5 in the first rotational direction (see arrow 36 in FIGS. 7 and 8A). Rotation of the dose member 5 is converted into axial movement of the drive member 21 in the proximal direction with respect to the housing 2 and with respect to the piston rod 14 by mechanical cooperation of the dose member 5 and the drive member 21 as described previously. Thereby, the interaction member 19 is displaced proximally by the dosing distance with respect to the housing 2 and with respect to the stop member 18. However, the interaction member 19 and the stop member 18 do not yet overlap and, thus, the inner surface of the drive member 21 prevents the stop member 18 from relaxing radially outwardly. The device 1 is in the non-locking mode.

Due to the splined connection of the dose member 5 and the first clicker means 26, the first clicker means 26 follows rotation of the dose member 5 (arrow 43, FIG. 8B). The second clicker means 22 follows rotation of the first clicker means 26 due to mechanical cooperation of the first clicker means 26 and the second clicker means 22 (arrow 44, FIG. 8B). As described previously, the third clicker means 23 is prevented from rotating. However, when the teeth 22A of the second clicker means 22 slide over the teeth 23A of the third clicker means 23, teeth 22A push the third clicker means 23 in the distal direction, as indicated by arrow 37 in FIG. 8B. The resilient member 24 pushes the third clicker means 23 proximally and, hence, back into its initial position with respect to the housing 2, as indicated by arrow 38 in FIG. 8B. An audible and/or tactile feedback may be given to the user when the next respective teeth 22A and 23A re-engage with each other.

The user may rotate the dose member 5 in the first rotational direction until a desired dose has been reached. When the maximum settable dose has been set, the dose member 5 may abut an annular stop member, thus being prevented from being rotated further in the first rotational direction. The set dose may be indicated, for example, in a window aperture (not explicitly shown), which may be arranged in the housing 2. If the dose member 5 was rotated too far, e.g. if the set dose exceeds the intended dose, the user may correct the set dose.

For this purpose, the user rotates the dose setting grip 7 and, hence, the dose member 5 in the second rotational direction with respect to the housing 2, as indicated by arrow 42 in FIG. 9A. As, during dose correction, the clutch connection of the drive member 21 and the dose member 5 is opened and, hence, the drive member 21 is prevented from being rotationally locked with the dose member 5, rotation of the dose member 5 is converted into distal movement of the drive member 21 with respect to the housing 2 and with respect to the piston rod 14. Accordingly, the interaction member 19 is displaced in the distal direction with respect to the stop member 18 by a distance smaller than the dosing distance. If the dose was set erroneously by the user, the interaction member 19 may be displaced in the distal direction with respect to the stop member 18 by the dosing distance. In particular, the interaction member 19 may resume it axial start position.

Again, the first clicker means 26 follows rotation of the dose member 5 (arrow 43 in FIG. 9B). Due to mechanical cooperation of the first clicker means 26 and the second clicker means 22, in particular due to the uni-directional clutch mechanism, the second clicker means 22 is prevented from following rotation of the first clicker means 26 in the second rotational direction. When the teeth 26A of the first clicker means 26 slide over the teeth 22B of the second clicker means 22, teeth 26A push the second clicker means 22 and, hence, the third clicker means 23 which is coupled to the second clicker means 22, in the distal direction, as indicated by arrow 44 in FIG. 9B. The resilient member 24 pushes the second clicker means 22 and the third clicker means 23 proximally and towards their initial position with respect to the housing 2, as indicated by arrow 45 in FIG. 9B. An audible and/or tactile feedback may be given to the user when the next respective teeth 22B and 26A engage with each other. The user may rotate the dose member 5 in the second rotational direction until the dose has been corrected, i.e. the desired dose has been reached or the dose has been unset.

FIGS. 9A and 9B schematically show a sectional view of the parts of the drug delivery device of FIG. 7 during dose dispensing.

For dispensing the set dose of the drug 12 the user pushes onto the dose button 6, which is indicated by arrow 41 in FIG. 9A. Because of the applied axial force, the spring member 25 is compressed and the teeth 30 of the drive member 21 and teeth 31 of the dose member 5 are brought into engagement with each other. Accordingly, the clutch connection between the drive member 21 and the dose member 5 is closed. Hence, the drive member 21 and the dose member 5 are rotationally locked. The drive member 21 and the dose member 5 are rotationally locked as long as the user keeps pressing onto the dose button 6.

The axial force applied onto the dose button 6 results in the rotation of the dose member 5 and, hence, of the drive member 21 in the second rotational direction with respect to the housing 2 and with respect to the dose button 6, in particular due to the non-self-locking threaded connection of the dose member 5 to the housing 2.

Rotation of the drive member 21 in the second rotational direction is converted into rotation of the piston rod 14 in the second rotational direction. The rotation of the piston rod 14 is converted into movement of the piston rod 14 in the distal direction with respect to the housing 2, e.g. by the threaded connection of the piston rod 14 and the housing 2. The piston rod 14 drives the bung 11 in the distal direction with respect to the cartridge 4 and, hence, the set dose of the drug 12 is dispensed from the cartridge 4. Thereby, the axial distance between the stop member 18 and the interaction member 19 is reduced.

Figure 10:
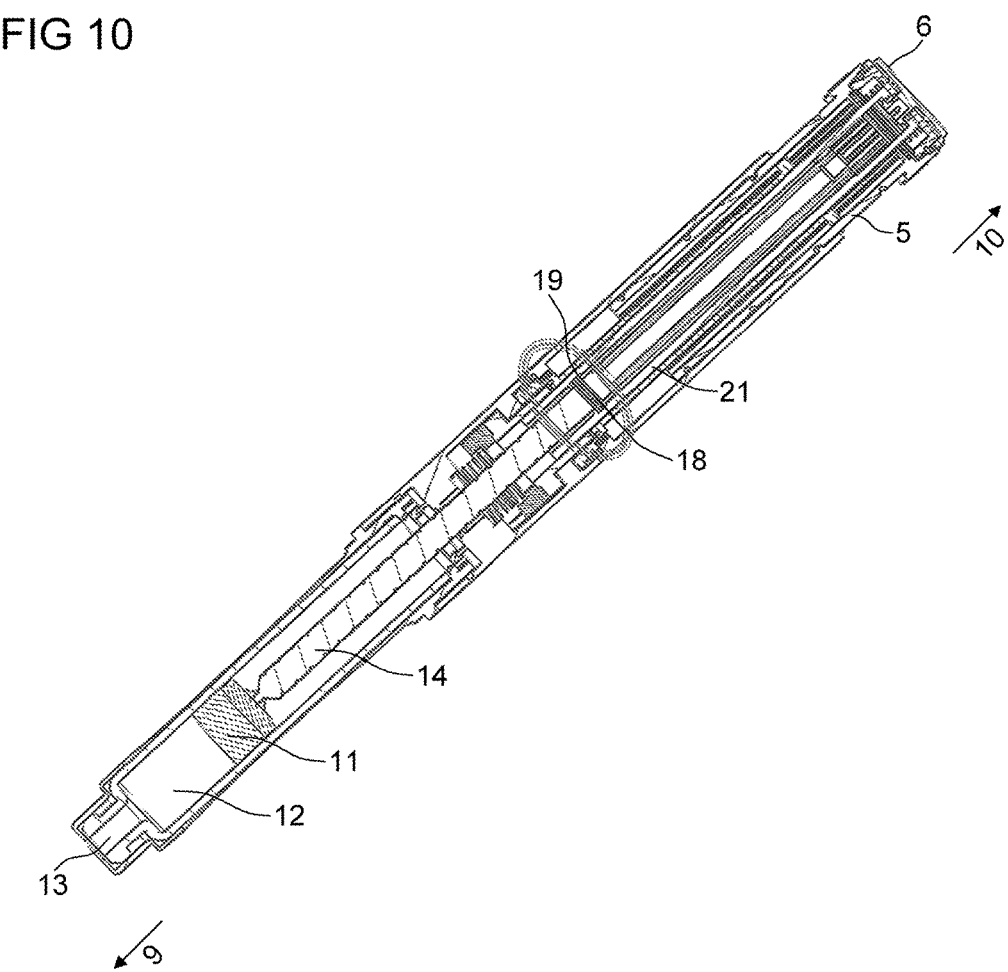

FIG. 10 schematically shows a sectional view of the drug delivery device of FIG. 1 after having set a last dose.

Figure 11:
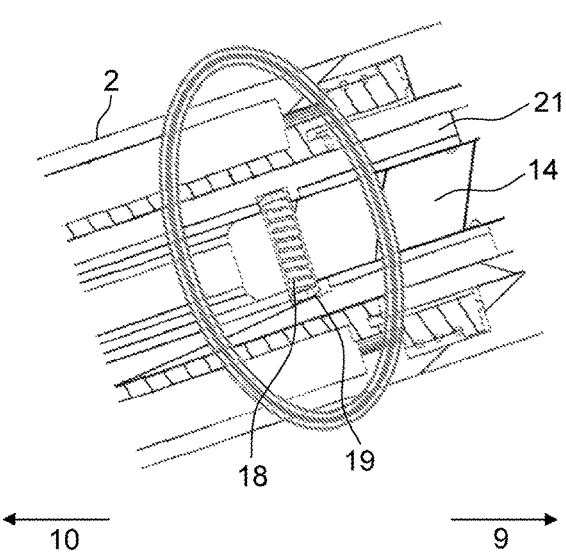

FIG. 11 schematically shows a sectional view of a part of the drug delivery device of FIG. 10.

Figure 12:
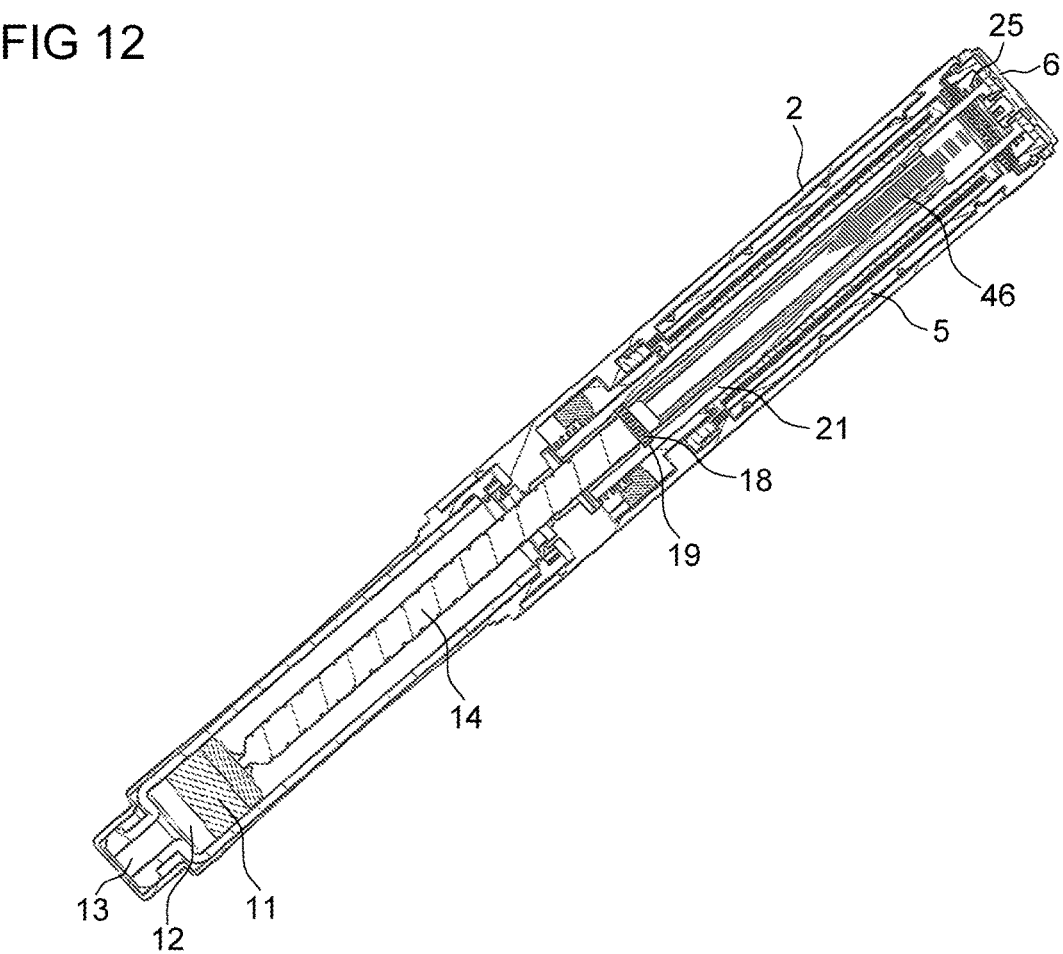

FIG. 12 schematically shows a sectional view of the drug delivery device of FIG. 10 after having dispensed the last dose.

The above described operation of setting, correcting and delivering the drug 12 is repeated until the maximum settable dose exceeds the quantity of drug still available in the device 1. In particular, after having set and delivered a subsequent dose of the drug 12, the piston rod 14 may have reached a distal end position, e.g. the bung 11 may have reached the most distal position in the cartridge 4.

When setting the subsequent dose of the drug 12, the drive member 21 and, thus, the interaction member 19, is again displaced by the dosing distance in the proximal direction with respect to the piston rod 14 (see FIG. 10) and, hence, with respect to the stop member 18, as already described in connection with FIGS. 7, 8A and 8B. However, at the end of this dose setting action, i.e. when the interaction member 19 has been displaced by the dosing distance, the interaction member 19 and the stop member 18 axially overlap (see in particular FIG. 11). Thus, the stop member 18 relaxes radially outwardly, thereby mechanically interacting with the interaction member 19. Accordingly, the device 1 is switched into the locking mode. Due to mechanical cooperation of the stop member 18 and the interaction member 19, the drive member 21 is prevented from being displaced further in the proximal direction with respect to the piston rod 14 as described in connection with FIG. 6.

After the last dose has been set, in particular when the drive member 21 is secured against proximal displacement with respect to the piston rod 14, a dose delivery action is performed to deliver the last dose (see arrow 46, FIG. 12). After having delivered the last dose, the bung 11 has reached the most distal position in the cartridge 4 (FIG. 12). If the device 1 is a re-usable drug delivery device, it may now be resetted for making the device 1 ready for setting and dispensing a plurality of doses of drug held in a replacement cartridge.

For resetting the drug delivery device 1, the cartridge holder 3 is unsecured from the housing 2. The emptied cartridge 4 is removed from the cartridge holder 3 and the replacement cartridge is introduced into the cartridge holder 3.

The piston rod 14 is rotated in the first rotational direction, thereby being displaced in the proximal direction with respect to the housing 2, i.e. in the direction opposite as indicated by arrow 46 in FIG. 12. In particular, the piston rod 14 is displaced towards and positioned in a proximal stop position with respect to the housing 2. When the piston rod 14 is displaced proximally, the stop member 18 and the interaction member 19 disengage, e.g. by mechanical cooperation of the stop member 18 and the oblique side face of the interaction member 19.

In the proximal stop position the piston rod 14 abuts at least one proximal stop member 15 (see FIG. 6), e.g. a flange protruding radially inwardly from the drive member 21. Proximal stop member 15 is arranged in the proximal end section of the drive member 21, for example. The drive member 21 follows rotation of the piston rod 14 in the first rotational direction. Due to mechanical cooperation of engaging means 53 and mating engaging means 54 (see FIGS. 13A and 13B) the dose button 6 is rotationally locked to the drive member 21 for resetting the device 1.

Alternatively, for resetting the device 1, instead of rotating the piston rod 14, the dose button 6 and, hence, the drive member 21 are rotated in the first rotational direction due to mechanical cooperation of engaging means 53 and mating engaging means 54 which enables the uni-directional coupling of the dose button 6 and the drive member 21. Rotation of the dose button 6 and of the drive member 21 is transferred into rotation of the piston rod 14 in the first rotational direction for resetting the device 1.

When the piston rod 14 is in the proximal stop position the cartridge holder 3 retaining the replacement cartridge is secured to the housing 2. Now, the device 1 is ready for setting and delivering the drug 12 held in the replacement cartridge.

The drug delivery device 1 described above may provide a high dose accuracy. The drug delivery device 1 may for example be configured for setting and delivering doses of 30 IU or greater, for example a dose of 50 IU or greater, thereby providing high dose accuracy. Alternatively, the drug delivery device 1 may provide doses of 5 IU or less or any dose in-between while having good dose accuracy.

Other implementations are within the scope of the following claims. Elements of different implementations may be combined to form implementations not specifically described herein.

The invention claimed is:

1. An assembly for a drug delivery device, comprising:
   a housing having a distal end and a proximal end,
   a piston rod,
   a drive member, the drive member being moveable in a proximal direction with respect to the housing and with respect to the piston rod for setting a dose of a drug,
   at least one stop member which is provided on one of the piston rod and the drive member and which is radially moveable with respect to the one of the piston rod and the drive member on which the at least on stop member is provided,
   at least one interaction member which is provided on the other one of the piston rod and the drive member,
   wherein, in a non-locking mode of the assembly, the stop member is radially biased, and the stop member and the interaction member are arranged axially spaced apart from each other by an axial distance, the axial distance being reduced by a dosing distance when the drive member is moved in the proximal direction, and
   wherein, when the dosing distance corresponds to the axial distance, the assembly is configured to switch into a locking mode, wherein, for switching into the locking mode, the radial bias of the stop member is permitted to decrease at least partially to bring the stop member and the interaction member in mechanical cooperation, wherein, when the stop member and the interaction member mechanically cooperate, the stop member and the interaction member are configured to axially interlock the piston rod and the drive member such that, in the locking mode,
   movement of the drive member in the proximal direction with respect to the piston rod is prevented;
   a dose setting action of the assembly is prevented due to mechanical cooperation of the stop member and the interaction member: and
   the piston rod and the drive member are releasably axially interlocked by mechanical cooperation of the interaction member and the stop member such that a dose correction action of the assembly is enabled in the locking mode.

2. The assembly according to claim 1, wherein the stop member comprises a resilient member or a resiliently mounted member, and wherein the interaction member comprises at least one cavity.

3. The assembly according to claim 1, wherein, if the at least one stop member is provided on the piston rod, the stop member is biased radially outwardly with respect to the housing when the assembly is in the non-locking mode, and wherein, if the at least one stop member is provided on the drive member, the stop member is biased radially inwardly with respect to the housing when the assembly is in the non-locking mode.

4. The assembly according to claim 1, wherein the assembly comprises a dose member, and, in the non-locking mode, the dose member is displaceable in the proximal direction with respect to the housing and with respect to the piston rod for setting the dose and displaceable in the distal direction with respect to the housing and with respect to the piston rod for correcting the set dose, wherein the drive member is arranged to follow displacement of the dose member with respect to the housing and with respect to the piston rod for setting and for correcting the dose.

5. The assembly according to claim 4, wherein the dose member is rotatable with respect to the housing, and wherein the dose member and the drive member are adapted to be releasably coupled to one another via a clutch connection, wherein, when the dose member and the drive member are decoupled, the dose member is rotatable with respect to the drive member for setting or correcting the dose, and wherein, when the dose member and the drive member are coupled, rotational movement of the dose member is converted into rotational movement of the drive member with respect to the housing.

6. The assembly according to claim 5, comprising a spring member which is adapted and arranged to keep the drive member and the dose member decoupled to permit relative rotational movement of the dose member and the drive member for setting or correcting the dose.

7. The assembly according to claim 5 further comprising a dose button, wherein the drive member and the dose button are adapted to be coupled to one another by a uni-directional rotational coupling, the uni-directional rotational coupling being configured to permit rotational movement of the drive member with respect to the dose button in one rotational direction when delivering the set dose and to prevent rotational movement of the drive member with respect to the dose button in the opposite rotational direction,
wherein the dose button is configured to be pushed for delivering the set dose such that the dose button is displaced in the distal direction with respect to the dose member for coupling the dose member and the drive member by the clutch connection.

8. The assembly according to claim 1, wherein the piston rod comprises a thread which is flattened in at least one axially extending portion and the drive member comprises at least one flattened portion provided axially along the inner surface of the drive member, wherein the piston rod is splined to the drive member by mechanical cooperation of the flattened inner portion and the flattened axially extending portion of the thread.

9. The assembly according to claim 1, wherein the interaction member comprises an oblique side face arranged in a proximal end section of the interaction member, the oblique side face being adapted and arranged to allow movement of the drive member in the distal direction with respect to the piston rod for correcting the set dose in the locking mode.

10. The assembly according to claim 1, wherein, when the drive member is moved in the distal direction with respect to the piston rod for correcting the set dose starting from the locking mode, the assembly is switched from the locking mode back into the non-locking mode.

11. The assembly according to claim 1, wherein, in the locking mode, the piston rod and the drive member are permanently axially interlocked by mechanical cooperation of the interaction member and the stop member such that a dose setting and a dose correction action is prevented in the locking mode.

12. The assembly according to claim 1, comprising a dose button, wherein the drive member and the dose button are adapted to be coupled to one another by a uni-directional rotational coupling, the uni-directional rotational coupling being configured to permit rotational movement of the drive member with respect to the dose button in one rotational direction when delivering the set dose and to prevent rotational movement of the drive member with respect to the dose button in the opposite rotational direction.

13. A drug delivery device comprising the assembly according to claim 1 and a cartridge, the cartridge holding a plurality of doses of a drug, wherein the assembly provides an end-stop mechanism preventing setting of a dose of the drug exceeding the dispensable quantity of the drug held in the cartridge.

14. A drug delivery device comprising the assembly according to claim 1 and further comprising a piston rod comprising a resiliently mounted member arranged in a proximal end section of the piston rod, the resiliently mounted member being radially moveable with respect to the piston rod.

15. An assembly for a drug delivery device, comprising:
a housing having a distal end and a proximal end,
a piston rod,
a dose member,
a drive member arranged to follow displacement of the dose member with respect to the housing and with respect to the piston rod for setting and for correcting the dose, the drive member being moveable in a proximal direction with respect to the housing and with respect to the piston rod for setting a dose of a drug,
at least one stop member which is provided on one of the piston rod and the drive member and which is radially moveable with respect to the one of the piston rod and the drive member on which it is provided,
at least one interaction member which is provided on the other one of the piston rod and the drive member,
wherein, in a non-locking mode of the assembly, the stop member is radially biased, and the stop member and the interaction member are arranged axially spaced apart from each other by an axial distance, the axial distance being reduced by a dosing distance when the drive member is moved in the proximal direction, and the dose member is displaceable in the proximal direction with respect to the housing and with respect to the piston rod for setting the dose and displaceable in the distal direction with respect to the housing and with respect to the piston rod for correcting the set dose, and
wherein, when the dosing distance corresponds to the axial distance, the assembly is configured to switch into a locking mode, wherein, for switching into the locking mode, the radial bias of the stop member is permitted to decrease at least partially to bring the stop member and the interaction member in mechanical cooperation, wherein, when the stop member and the interaction member mechanically cooperate, the stop member and the interaction member are configured to axially interlock the piston rod and the drive member such that, in the locking mode, movement of the drive member in the proximal direction with respect to the piston rod is prevented.

16. An assembly for a drug delivery device, comprising:
a housing having a distal end and a proximal end,
a piston rod comprising a thread which is flattened in at least one axially extending portion,
a drive member comprises at least one flattened portion provided axially along the inner surface of the drive member, the drive member being moveable in a proximal direction with respect to the housing and with respect to the piston rod for setting a dose of a drug,
at least one stop member which is provided on one of the piston rod and the drive member and which is radially moveable with respect to the one of the piston rod and the drive member on which it is provided,
at least one interaction member which is provided on the other one of the piston rod and the drive member,
wherein, in a non-locking mode of the assembly, the stop member is radially biased, and the stop member and the interaction member are arranged axially spaced apart from each other by an axial distance, the axial distance being reduced by a dosing distance when the drive member is moved in the proximal direction,
wherein, when the dosing distance corresponds to the axial distance, the assembly is configured to switch into a locking mode, wherein, for switching into the locking mode, the radial bias of the stop member is permitted to decrease at least partially to bring the stop member and the interaction member in mechanical cooperation, wherein, when the stop member and the interaction member mechanically cooperate, the stop member and the interaction member are configured to axially interlock the piston rod and the drive member such that, in the locking mode, movement of the drive member in the proximal direction with respect to the piston rod is prevented, and wherein the piston rod is splined to the drive member by mechanical cooperation of the flattened inner portion and the flattened axially extending portion of the thread.

17. An assembly for a drug delivery device, comprising:
a housing having a distal end and a proximal end,
a piston rod,
a dose button,
a drive member, the drive member being moveable in a proximal direction with respect to the housing and with respect to the piston rod for setting a dose of a drug,
at least one stop member which is provided on one of the piston rod and the drive member and which is radially moveable with respect to the one of the piston rod and the drive member on which it is provided,
at least one interaction member which is provided on the other one of the piston rod and the drive member,
wherein, in a non-locking mode of the assembly, the stop member is radially biased, and the stop member and the interaction member are arranged axially spaced apart from each other by an axial distance, the axial distance being reduced by a dosing distance when the drive member is moved in the proximal direction, wherein the drive member and the dose button are adapted to be coupled to one another by a uni-directional rotational coupling, the uni-directional rotational coupling being configured to permit rotational movement of the drive member with respect to the dose button in one rotational direction when delivering the set dose and to prevent rotational movement of the drive member with respect to the dose button in the opposite rotational direction, and wherein, when the dosing distance corresponds to the axial distance, the assembly is configured to switch into a locking mode, wherein, for switching into the locking mode, the radial bias of the stop member is permitted to decrease at least partially to bring the stop member and the interaction member in mechanical cooperation, wherein, when the stop member and the interaction member mechanically cooperate, the stop member and the interaction member are configured to axially interlock the piston rod and the drive member such that, in the locking mode, movement of the drive member in the proximal direction with respect to the piston rod is prevented.

* * * * *